United States Patent [19]

Brinkman et al.

[11] 4,089,945
[45] May 16, 1978

[54] ANTIDANDRUFF SHAMPOOS CONTAINING METALLIC CATION COMPLEX TO REDUCE IN-USE SULFIDE ODOR

[75] Inventors: Richard Edward Brinkman, Montgomery; Robert Loren Vogenthaler, Cincinnati, both of Ohio

[73] Assignee: The Procter & Gamble Company, Cincinnati, Ohio

[21] Appl. No.: 757,190

[22] Filed: Jan. 6, 1977

Related U.S. Application Data

[63] Continuation-in-part of Ser. No. 591,978, Jun. 30, 1975, abandoned.

[51] Int. Cl.² ............................................. A61K 33/04
[52] U.S. Cl. ................................. 424/164; 252/106; 252/107; 424/162; 424/288; 424/290; 424/291; 424/292; 424/293; 424/294; 424/296; 424/297
[58] Field of Search ............... 424/DIG. 4, 164, 162, 424/288, 290, 291, 292, 293, 294, 296, 297; 252/106, 107

[56] References Cited

U.S. PATENT DOCUMENTS

| 2,694,669 | 11/1954 | Baldwin et al. | 424/164 |
|---|---|---|---|
| 2,884,352 | 4/1959 | Brenner et al. | 424/164 |
| 2,933,432 | 4/1960 | Lichtin | 424/131 |
| 3,071,514 | 1/1963 | Phillips et al. | 424/131 |
| 3,086,943 | 4/1963 | Lang | 424/70 X |
| 3,126,313 | 3/1964 | Johnson | 424/164 |
| 3,152,046 | 10/1964 | Kapral | 424/164 |
| 3,236,733 | 2/1966 | Karsten et al. | 424/245 |
| 3,398,227 | 8/1968 | Every et al. | 424/162 |
| 3,476,489 | 11/1969 | Mees et al. | 424/164 |
| 3,580,853 | 5/1971 | Parran | 424/70 |

FOREIGN PATENT DOCUMENTS

| 829,426 | 3/1960 | United Kingdom | 424/164 |

OTHER PUBLICATIONS

Gattesfoss, R. M., Soap, Perfumery & Cosmetics, vol. 15, (1942), pp. 43–45.
Neesby, American Perfumer & Aromatics, vol. 73–74, (1959) pp. 38, 40–42.
Bergwein, Dragoco Report, vol. 5–7, (1958–1960), pp. 78–80.
Colloidal Sulfur, Technical Leaflet, Badische Anilin & Soda–Fabrik AG, (1968), 2 pp.
Harry, Modern Cosmeticology, N. Y., Chemical Publishing Co., (1953), pp. 338–339.
Jocelyn, Biochemistry of SH Group, Academic Press, New York, (1972), pp. 79–93.

*Primary Examiner*—Albert T. Meyers
*Assistant Examiner*—Vera C. Clarke
*Attorney, Agent, or Firm*—Douglas C. Mohl; John A. O'Toole; Richard C. Witte

[57] ABSTRACT

An antidandruff shampoo comprising a surfactant, sulfur or selenium sulfide and a metallic complex wherein the cation of said complex is an ion of a heavy metal and the complexing agent is selected so that the complex can effectively counteract the formation of sulfide off odors.

10 Claims, No Drawings

ANTIDANDRUFF SHAMPOOS CONTAINING METALLIC CATION COMPLEX TO REDUCE IN-USE SULFIDE ODOR

CROSS REFERENCE TO RELATED APPLICATION

This application is a continuation-in-part application of our copending application Ser. No. 591,978 filed June 30, 1975, now abandoned entitled "ANTIDANDRUFF SHAMPOO.

BACKGROUND OF THE INVENTION

1. Field of the Invention

The present invention relates to antidandruff shampoos which contain sulfur or selenium sulfide but do not develop serious sulfide off odors during use because of the presence of a metallic complex.

2. Prior Art

Dandruff is a common afflication frequently associated with the human scalp area. It is recognized that skin normally sloughs off the skin surfaces of the human body. On most areas of the body, the skin which is sloughed off is normally washed away at frequent intervals so that it is not noticeable. On the scalp, which is not normally washed as often as other parts of the body, the sloughed off skin tends to accumulate. This accumulation is noticeable as dandruff flakes and, in combination with the natural oils exuded by the scalp, forms a suitable environment for the growth of microorganisms.

Not surprisingly, there have been numerous attempts to formulate products which would effectively counteract the formation of dandruff. Included in the group of antidandruff agents which have been used in these formulations are sulfur, salicylic acid, hexachlorophene, resorcinol, tar, selenium sulfide and zinc pyrithione. Sulfur, particularly, has long been recognized as a suitable ingredient for a number of cosmetic products including shampoos. Such uses are disclosed in "Sulphur in Therapeutics and as an Active Substance in Cosmetics," Dragoco Report, Vols. 5-7, pp. 78-80, (1958-1960) and "Sulphur in Cosmetics and Dermato-Therapeutics," *American Perfumer & Aromatics,* Vols. 73-74, pp. 38 and 40-42, (1959). Sulfur's use in shampoos is also shown in U.S. Pat. No. 3,476,489, Nov. 4, 1969, to Mees et al. and U.S. Pat. No. 2,884,352, Apr. 28, 1959, to Brenner et al.

Although sulfur has been used extensively in cosmetic products, its use has not been entirely satisfactory. One major problem associated with its use in shampoos has been the generation of sulfide off odors during the shampooing process and, often, of residual sulfide off odors for days afterwards. Selenium sulfide also suffers from this sulfide off odor problem. It has now been found that both initial and residual sulfide off odors can be alleviated by including a complex of a metallic cation in the sulfur or selenium sulfide-containing formulation.

It is, therefore, an object of this invention to provide a superior sulfur or selenium sulfide-containing shampoo product.

It is another object of this invention to provide an improved process for shampooing the hair to reduce dandruff.

SUMMARY OF THE INVENTION

The present invention relates to antidandruff shampoos containing metallic cation complexes which effectively counteracts the sulfide off odor during and after lathering. Such compositions comprise:

(A) from about 10% to about 50% of a surfactant;
(B) from about 1% to about 15% of an antidandruff agent which can be either elemental sulfur or selenium sulfide; and
(C) from about 0.1% to about 1% of a complex of a metallic cation and a complexing agent.

The cation can be selected from the group consisting of arsenic, mercury, copper, tin, bismuth, antimony, cadmium, lead, silver or gold. The complexing agent can be selected from the group consisting of amino-N-polycarboxylic acids, amino-N-carboxylic acids, polyamino-N-carboxylic acids, polycarboxylic acids, polyhydric monocarboxylic acids and polyamines.

DETAILED DESCRIPTION OF THE INVENTION

The odor blocking antidandruff shampoo compositions of the present invention essentially comprise a surfactant, an antidandruff agent and a metallic cation complex capable of preventing the formation of sulfide off odors. Each of these ingredients as well as optional components and composition preparation and use are discussed in detail as follows:

SURFACTANT

One essential component of the antidandruff shampoos herein is a surfactant. The term "surfactant" as used herein is intended to denote soap and nonsoap surfactants. The surfactant component comprises from about 10% to about 50% by weight of the composition, preferably 10% to about 20%.

Any nonsoap surfactant is suitable for use including anionic, nonionic, amphoteric and zwitterionic types. Cationic surfactants may also be used, but these are not preferred in the formulas of the present invention due to their irritation potential.

Examples of suitable soaps are the sodium, potassium, ammonium and alkanol ammonium salts of higher fatty acids (those having 10-20 carbon atoms). Anionic nonsoap surfactants can be exemplified by the alkali metal salts of organic sulfuric reaction products having in their molecular structure an alkyl radical containing from 8-22 carbon atoms and a sulfonic acid or sulfuric acid ester radical (included in the term alkyl is the alkyl portion of higher acyl radicals). Preferred are the sodium, potassium or triethanol amine alkyl sulfates, especially those obtained by sulfating the higher alcohols ($C_8$-$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms; sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine — products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodexocy-2-hydroxypropyldi(3-hydroxypropyl)amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are:
dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contains alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:
octadecyl methyl sulfoxide,
2-ketotridecyl methyl sulfoxide,
3,6,9-trioxaoctadecyl 2-hydroxyethyl sulfoxide,
dodecyl methyl sulfoxide,
oleyl 3-hydroxypropyl sulfoxide,
tetradecyl methyl sulfoxide,
3-methoxytridecyl methyl sulfoxide,
3-hydroxytridecyl methyl sulfoxide,
3-hydroxy-4-dodecoxybutyl methyl sulfoxide.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

$$R^2-\overset{(R^3)_x}{Y^{(+)}}-CH_2-R^4-Z^{(-)}$$

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; x is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.
Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-(P,P-dimethyl-P-dodecylphosphonio)-propane-1-phosphonate; and
5-[N,N-di(3-hydroxypropyl)-N-hexadecylammonio]-2-hydroxypentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g, carboxy, sulfonate, sulfate, phosphate, or phosphonate. Examples of compounds falling within this definition are sodium 3-dodecylaminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Many cationic surfactants are known to the art. By way of example, the following may be mentioned:
dodecyltrimethylammonium chloride;
nonylbenzylethyldimethylammonium nitrate;
tetradecylpyridinium bromide;
laurylpyridinium chloride;
cetylpyridinium chloride;
laurylpyridinium chloride;
laurylisoquinolium bromide; and
dilauryldimethylammonium chloride.

Many additional nonsoap surfactants are described in *McCutcheon's, Detergents and Emulsifiers,* 1976 *Annual,* published by Allured Publishing Corporation, which is incorporated herein by reference.

The above-mentioned surfactants can be used alone or in combination in the compositions of the present invention.

ANTIDANDRUFF AGENT

The instant compositions also essentially comprise from about 1% to about 15% by weight of an antidandruff agent selected from the group consisting of elemental sulfur and selenium sulfide. When the antidandruff agent is elemental sulfur, the instant shampoo compositions preferably comprise from about 2% to about 6% antidandruff agent.

The sulfur which is suitable for use herein can be any form of elemental sulfur. It is understood, of course, that the sulfur while being in elemental form may be sulfur which has been physically mixed with protective colloids such as gum arabic or dispersing agents such as surfactants or subjected to processing steps to modify its particle size or other physical property. Sulfur is available commercially in a variety of forms such as colloidal, micronized, sublimed, precipitated, and commercial flour. It is preferred that the sulfur used have a particle size of less than about 10 microns. A most preferred sulfur is "Colloidal Sulphur" supplied by BASF-Wyandotte. This material is in the form of spherical particles with a diameter of ½ to 2 microns and differs from other sulfur types in having from about 10 to about 15% entrapped water. The use of this particular sulfur in shampoos is disclosed in the application of Robert L. Vogenthaler, Ser. No. 591,977, filed June 30, 1975, now abandoned in favor of continuation application, Ser. No. 836,101, filed Sept. 23, 1977.

Selenium sulfide has been used in antidandruff shampoos for a number of years. Dispersions of selenium disulfide for use in shampoos is disclosed in U.S. Pat. No. 3,152,046, Oct. 6, 1964, to Kapral, said patent incorporated herein by reference.

METALLIC CATION COMPLEX

Another essential component of the present invention is a metallic cation complex which is essential to achieve the present invention's odor blocking properties. Metallic cation complexes generally comprise from about 0.1% to about 2% by weight of the compositions herein, preferably from about 0.2% to about 0.75% by weight.

The metallic cation complex has a metallic ion selected from the group consisting of arsenic, mercury, copper, tin, bismuth, antimony, cadmium, lead, silver and gold, while the complexing agent is one which is capable of forming a stable complex with said metallic cation. The stability of said complex must be such that the metallic cation can be available to block the formation of the sulfide off odors. Examples of suitable complexing agents are amino-N-polycarboxylic acids such as nitrilotriacetic acid and N-2-hydroxyethyl nitrilodiacetic acid; polyamino-N-polycarboxylic acids such as ethylene-diaminetetraacetic acid and hydroxyethylenediamine-triacetic acid, or their partially neutralized alkali metal, alkaline earth, ammonium or substituted ammonium salts; amino-N-carboxylic acids such as glycine; polyhydric monocarboyxlic acids such as gluconic acid; polycarboxylic acids such as citric acid, tartaric acid and succinic acid or their partially neutralized alkali metal, alkaline earth, ammonium or substituted ammonium salts; and polyamines such as ethylenediamine, propylenediamine, trimethylenediamine, triethylenetetraamine, N-2-hydroxyethylethylenediamine and N-hydroxyethylethylenediamine. Examples of substituted ammonium salts are those wherein one or more of the hydrogens on the ammonium cation are replaced by a $C_1$ to $C_3$ alkyl or hydroxyalkyl radical, e.g., mono-, di- or triethylammonium and mono-, di- or triethanolammonium. There are many other complexing agents which are appropriate for use in the complexes of the invention which are known to those skilled in the art.

The complexes of copper are preferred in the compositions of this invention. Most preferred are the copper complexes of amino-N-polycarboxylic, polyamino-N-polycarboxylic acids and polycarboxylic acids. A most preferred complex is the copper complex of ethylenediaminetetraacetic acid.

AQUEOUS CARRIER

The shampoos herein are preferably in the form of liquids or creams in which water is the principal diluent. The level of water in the compositions is typically from about 35% to about 89% by weight.

The pH of the shampoo compositions herein should lie in the range of about 3.0 to about 9.0, preferably in the range of about 4.0 to about 6.0. The pH can be adjusted to the desired level by using conventional pH adjusting agents such as those described hereinbelow.

OPTIONAL COMPONENTS

The antidandruff shampoos herein can contain a variety of non-essential optional ingredients suitable for rendering such compositions more aesthetically desirable. Such conventional optional ingredients are well known to those skilled in the art, e.g., preservatives such as benzyl alcohol, methyl paraben, propyl paraben and imidazolidinyl urea, thickeners and viscosity modifiers such as coconut ethanol amide, sodium chloride, sodium sulfate, carboxymethylcellulose, methylcellulose, polyvinyl alcohol, and ethyl alcohol; pH adjusting agents such as citric acid, succinic acid, phosphoric acid, sodium hydroxide, sodium carbonate, etc.; suspending agents such as magnesium/aluminum silicate; perfumes; dyes; opacifiers such as behenic acid and calcium stearate; and, sequestering agents such as disodium ethylenediamine tetraacetate.

PERFUMES, DYES, AND COLORING AGENTS

Minor ingredients such as perfumes, dyes and coloring agents can be added to the instant compositions to improve the consumer acceptability of the instant antidandruff shampoos. If present, such agents generally comprise from about 0.1% to 2.0% by weight of the composition.

COMPOSITION PREPARATION

The shampoo products of the present invention are made using mixing techniques which are well known in the art. A preferred means is to disperse the thickening agent, if one is used in the composition, in water with the other ingredients being added using simple mixing. The final composition is then subjected to high shear milling to ensure uniform dispersion of the shampoo components.

COMPOSITION USE

In its method aspect, the present invention comprises a method of shampooing the hair by contacting the hair with an amount of the shampoo compositions herein which is effective to clean the hair and reduce the amount of dandruff and rinsing the shampoo from the hair. An effective amount for any individual will depend upon variable factors such as length of the hair, thickness of the hair, amount of soil present, level of surfactant in the shampoo composition, etc. Generally, an effective amount will be from about 5 to about 40 grams per use.

The following examples will illustrate the invention, but are not intended to be in any way limiting thereof. All percentages used herein are by weight unless otherwise designated.

EXAMPLE I

The following shampoo was prepared as indicated previously.

| Component | Percent by Weight |
| --- | --- |
| Triethanolamine coconut alkyl sulfate (35% solution in water) | 55.00 |
| Colloidal sulfur water slurry (41.5% solution) | 9.64 |
| Methylcellulose | 0.35 |
| Coconut ethanol amide | 2.75 |
| Magnesium/aluminum silicate (5% solution in water) | 15.00 |

-continued

| Component | Percent by Weight |
| --- | --- |
| Methyl paraben | 0.20 |
| Propyl paraben | 0.10 |
| Imidazolidinyl urea | 0.30 |
| FD&C Blue Dye No. 1 | 0.40 |
| Succinic acid | 1.25 |
| Perfume | 1.00 |
| Disodium cupric ethylenediaminetetraacetate | 0.50 |
| Distilled water | 13.51 |

Shampooing of the hair in the normal manner with this shampoo results in a very low degree of "sulfide type" odor during lathering and after shampooing of the hair. The hair is left clean and lustrous after drying.

EXAMPLE II

The following shampoo composition was prepared in the same manner as that of Example I.

| Component | Percent by Weight |
| --- | --- |
| Sodium lauryl sarcosinate | 4.0 |
| Colloidal sulfur | 4.0 |
| Sodium chloride | 6.0 |
| Sodium coconut alkyl glyceryl sulfonate | 30.0 |
| N-cocoyl sarcosine | 0.7 |
| FD&C Blue Dye No. 1 | 0.4 |
| Perfume | 0.5 |
| Succinic acid | 1.0 |
| Disodium cupric ethylenediaminetetraacetate | 0.5 |
| Distilled water | q.s. 100.0 |

What is claimed is:

1. A shampoo composition comprising in an aqueous carrier:
   (A) from about 10% to about 50% of a surfactant;
   (B) from about 1% to about 15% of an antidandruff agent selected from the group consisting of elemental sulfur and selenium sulfide; and
   (C) from about 0.1% to about 1% of a complex of a metallic cation wherein the metal is selected from the group consisting of arsenic, mercury, copper, tin, bismuth, antimony, cadmium, lead, silver and gold and the complexing agent is selected from the group consisting of amino-N-polycarboxylic acids, amino-N-carboxylic acids, polyamino-N-carboxylic acids, polycarboxylic acids, polyhydric monocarboxylic acids and polyamines.

2. The shampoo composition of claim 1 wherein component (B) is present at a level of from about 2% to about 6% and component (C) is present at a level of from about 0.2% to about 0.75%.

3. The shampoo composition of claim 2 wherein component (A) is selected from the group consisting of anionic, nonionic, amphoteric, zwitterionic surfactants and mixtures of these.

4. The shampoo composition of claim 3 wherein the metallic cation of component C is a copper ion.

5. The shampoo composition of claim 4 wherein the pH is from about 4 to about 6.

6. The shampoo composition of claim 5 wherein component (C) is a complex of copper and a complexing agent selected from the group consisting of amino-N-polycarboxylic acids, amino-N-carboxylic acids, polyamino-N-polycarboxylic acids, polycarboxylic acids and polyhydric monocarboxylic acids.

7. The shampoo composition of claim 6 wherein component (C) is a copper complex of ethylenediaminetetraacetic acid.

8. The shampoo composition of claim 6 wherein component (C) is a copper complex of citric acid.

9. The shampoo composition of claim 6 wherein component (C) is a copper complex of gluconic acid.

10. The shampoo composition of claim 6 wherein component (C) is a copper complex of glycine.

* * * * *